United States Patent
Ennett-Shepard

(10) Patent No.: US 10,189,818 B2
(45) Date of Patent: Jan. 29, 2019

(54) 5-(5-(2-(3-AMINOPROPDOXY)-6-METHOXY-PHENYL)-1H-PYRAZOL-3-YLAMINO)PYRA-ZINE-2-CARBONITFILE (S)-LACTATE MONOHYDRATE

(71) Applicant: Eli Lilly and Company, Indianapolis, IN (US)

(72) Inventor: Alessandra B. Ennett-Shepard, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 127 days.

(21) Appl. No.: 15/513,185

(22) PCT Filed: Dec. 1, 2016

(86) PCT No.: PCT/US2016/064379
§ 371 (c)(1),
(2) Date: Mar. 22, 2017

(87) PCT Pub. No.: WO2017/100071
PCT Pub. Date: Jun. 15, 2017

(65) Prior Publication Data
US 2018/0230132 A1 Aug. 16, 2018

Related U.S. Application Data

(60) Provisional application No. 62/263,908, filed on Dec. 7, 2015.

(51) Int. Cl.
*C07D 403/12* (2006.01)
*A61P 35/00* (2006.01)

(52) U.S. Cl.
CPC ............ *C07D 403/12* (2013.01); *A61P 35/00* (2018.01)

(58) Field of Classification Search
CPC ............................ C07D 403/12; A61K 35/00
USPC ...................................... 514/254.05
See application file for complete search history.

(56) References Cited

U.S. PATENT DOCUMENTS 8,314,108 B2    11/2012 Farouz et al.

OTHER PUBLICATIONS

NIH—National Cancer Institute "Clinical Trials Using Prexasertib" https://www.cancer.gov/about-cancer/treatment/clinical-trials/intervention/prexasertib (Year: 2018).*

* cited by examiner

*Primary Examiner* — Yevgeny Valenrod
(74) *Attorney, Agent, or Firm* — Elizabeth Dingess-Hammond; James B. Myers

(57) ABSTRACT

The disclosure herein includes 5-(5-(2-(3-aminopropoxy)-6-methoxyphenyl)-1H-pyrazol-3-ylamino)pyrazine-2-carbonitrile (S)-lactate monohydrate that inhibits Chk1/2 and is useful in the treatment of cancer.

13 Claims, No Drawings

5-(5-(2-(3-AMINOPROPDOXY)-6-METHOXY-PHENYL)-1H-PYRAZOL-3-YLAMINO)PYRAZINE-2-CARBONITFILE (S)-LACTATE MONOHYDRATE

The present invention relates to 5-(5-(2-(3-aminopropoxy)-6-methoxyphenyl)-1H-pyrazol-3-ylamino)pyrazine-2-carbonitrile (S)-lactate monohydrate, that inhibits checkpoint kinase 1 (hereafter, Chk1) and checkpoint kinase 2 (hereafter, Chk2) and is useful for treating cancers, particularly those characterized by defects in deoxyribonucleic acid (DNA) replication, chromosome segregation, or cell division.

In mammalian cells, Chk1 is phosphorylated and activated in response to agents that cause DNA damage including, but not limited to, ionizing radiation (IR), ultraviolet (UV) light, and hydroxyurea. Chk1 phosphorylation may lead to cellular arrest in S phase and/or at G2/M. DNA damage can also result in the activation of Chk2 which can also promote cell cycle arrest.

Because of Chk1's and Chk2's role in DNA damage repair, inhibitors of Chk1/2 have received interest for use in treating cancer. U.S. Pat. No. 8,314,108, for example, discloses the Chk1/2 inhibitors 5-(5-(2-(3-aminopropoxy)-6-methoxyphenyl)-1H-pyrazol-3-ylamino)pyrazine-2-carbonitrile, 5-(5-(2-(3-aminopropoxy)-6-methoxyphenyl)-1H-pyrazol-3-ylamino)pyrazine-2-carbonitrile formic acid salt, 5-(5-(2-(3-aminopropoxy)-6-methoxyphenyl)-1H-pyrazol-3-ylamino)pyrazine-2-carbonitrile dihydrogen chloride salt, 5-(5-(2-(3-aminopropoxy)-6-methoxyphenyl)-1H-pyrazol-3-ylamino)pyrazine-2-carbonitrile methanesulfonic acid salt, and 5-(5-(2-(3-aminopropoxy)-6-methoxyphenyl)-1H-pyrazol-3-ylamino)pyrazine-2-carbonitrile methanesulfonic acid monohydrate salt.

However, there is still a need for aminopyrazole compounds that not only inhibit Chk1/2, but that have properties that facilitate commercialization and improve the dosing experience for the patient. For example, some aminopyrazole compounds incur physical changes over time when in formulation. Such changes may reduce the amount of active ingredient in the formulation, leading to a potential decrease in efficacy. Others may be poorly soluble and require solubilization agents and/or an increase in the number of vials for proper dosing. The formulation of some of these aminopyrazole compounds may also result in high levels of impurities, dimerization in the solid state, and/or rather large particle sizes. Others may require longer lyophilization times, increasing the risk to the quality of the finished product.

The present invention provides a novel, pharmaceutically acceptable salt of an aminopyrazole compound that inhibits Chk1/2 and provides several advantages over previously disclosed aminopyrazole compounds.

The present invention provides a compound which is 5-(5-(2-(3-aminopropoxy)-6-methoxyphenyl)-1H-pyrazol-3-ylamino)pyrazine-2-carbonitrile (S)-lactate monohydrate. The present invention also provides 5-(5-(2-(3-aminopropoxy)-6-methoxyphenyl)-1H-pyrazol-3-ylamino)pyrazine-2-carbonitrile (S)-lactate monohydrate in isolation.

The present invention provides 5-(5-(2-(3-aminopropoxy)-6-methoxyphenyl)-1H-pyrazol-3-ylamino)pyrazine-2-carbonitrile (S)-lactate monohydrate in crystalline form. The present invention also provides 5-(5-(2-(3-aminopropoxy)-6-methoxyphenyl)-1H-pyrazol-3-ylamino)pyrazine-2-carbonitrile (S)-lactate monohydrate in crystalline form characterized by an X-ray powder diffraction pattern (CuKa radiation, λ=1.54060 Å) comprising a peak at 12.6, and one or more peaks at 24.8, 25.5, 8.1, 6.6, 12.3, and 16.3 (2θ+/−0.2°).

The present invention provides a pharmaceutical composition comprising 5-(5-(2-(3-aminopropoxy)-6-methoxyphenyl)-1H-pyrazol-3-ylamino)pyrazine-2-carbonitrile (S)-lactate monohydrate and one or more of a pharmaceutically acceptable carrier, diluent, or excipient.

The present invention provides a method of treating cancer, comprising administering to a patient in need thereof an effective amount of 5-(5-(2-(3-aminopropoxy)-6-methoxyphenyl)-1H-pyrazol-3-ylamino)pyrazine-2-carbonitrile (S)-lactate monohydrate. In addition, the present invention also provides a method of treating cancer, comprising administering to a patient in need thereof an effective amount of 5-(5-(2-(3-aminopropoxy)-6-methoxyphenyl)-1H-pyrazol-3-ylamino)pyrazine-2-carbonitrile (S)-lactate monohydrate and ionizing radiation. The present invention provides a method of treating cancer, comprising administering to a patient in need thereof an effective amount of 5-(5-(2-(3-aminopropoxy)-6-methoxyphenyl)-1H-pyrazol-3-ylamino)pyrazine-2-carbonitrile (S)-lactate monohydrate and one or more chemotherapy agents. The present invention provides a method of treating cancer, comprising administering to a patient in need thereof an effective amount of 5-(5-(2-(3-aminopropoxy)-6-methoxyphenyl)-1H-pyrazol-3-ylamino)pyrazine-2-carbonitrile (S)-lactate monohydrate, one or more chemotherapy agents, and ionizing radiation.

The present invention provides the use of 5-(5-(2-(3-aminopropoxy)-6-methoxyphenyl)-1H-pyrazol-3-ylamino)pyrazine-2-carbonitrile (S)-lactate monohydrate for the manufacture of a medicament for the treatment of cancer. In addition, the present invention also provides the use of 5-(5-(2-(3-aminopropoxy)-6-methoxyphenyl)-1H-pyrazol-3-ylamino)pyrazine-2-carbonitrile (S)-lactate monohydrate for the manufacture of a medicament for the treatment of cancer wherein said treatment comprises combination therapy with ionizing radiation. The present invention provides the use of 5-(5-(2-(3-aminopropoxy)-6-methoxyphenyl)-1H-pyrazol-3-ylamino)pyrazine-2-carbonitrile (S)-lactate monohydrate for the manufacture of a medicament for the treatment of cancer by combination therapy wherein said combination therapy treatment comprises administration of said medicament and administration of one or more other chemotherapy agents to the same patient. The present invention provides the use of 5-(5-(2-(3-aminopropoxy)-6-methoxyphenyl)-1H-pyrazol-3-ylamino)pyrazine-2-carbonitrile (S)-lactate monohydrate for the manufacture of a medicament for the treatment of cancer by combination therapy wherein said combination therapy treatment comprises administration of said medicament and administration of one or more other chemotherapy agents and ionizing radiation to the same patient.

The present invention provides 5-(5-(2-(3-aminopropoxy)-6-methoxyphenyl)-1H-pyrazol-3-ylamino)pyrazine-2-carbonitrile (S)-lactate monohydrate for use in therapy. The present invention also provides 5-(5-(2-(3-aminopropoxy)-6-methoxyphenyl)-1H-pyrazol-3-ylamino)pyrazine-2-carbonitrile (S)-lactate monohydrate for use in the treatment of cancer. In addition, the present invention also provides 5-(5-(2-(3-aminopropoxy)-6-methoxyphenyl)-1H-pyrazol-3-ylamino)pyrazine-2-carbonitrile (S)-lactate monohydrate for use in simultaneous, separate, or sequential combination with ionizing radiation in the treatment of cancer. Furthermore, the present invention provides 5-(5-(2-(3-aminopropoxy)-6-methoxyphenyl)-1H-pyrazol-3-ylamino)pyrazine-2-carbonitrile (S)-lactate monohydrate for use in simultaneous, separate, or sequential combination with one or more chemotherapy agents in the treatment of cancer. In addition, the present invention also provides 5-(5-(2-(3-aminopropoxy)-6-methoxyphenyl)-1H-pyrazol-3-ylamino)pyrazine-2-carbonitrile (S)-lactate monohydrate for use in simultaneous, separate, or sequential combination with ionizing radiation in therapy. Furthermore, the present invention provides 5-(5-(2-(3-aminopropoxy)-6-methoxyphenyl)-1H-pyrazol-3-ylamino)pyrazine-2-carbonitrile (S)-lactate monohydrate for use in simultaneous, separate, or sequential combination with one or more chemotherapy agents for therapy. Furthermore, the present invention provides 5-(5-(2-(3-aminopropoxy)-6-methoxyphenyl)-1H-pyrazol-3-ylamino)pyrazine-2-carbonitrile (S)-lactate monohydrate for use in simultaneous, separate, or sequential combination with one or more chemotherapy agents and ionizing radiation for therapy.

The present invention provides use of 5-(5-(2-(3-aminopropoxy)-6-methoxyphenyl)-1H-pyrazol-3-ylamino)pyrazine-2-carbonitrile (S)-lactate monohydrate for the manufacture of a medicament for the treatment of cancer, wherein the medicament is to be administered simultaneously, separately or sequentially with ionizing radiation.

The present invention provides use of 5-(5-(2-(3-aminopropoxy)-6-methoxyphenyl)-1H-pyrazol-3-ylamino)pyrazine-2-carbonitrile (S)-lactate monohydrate for the manufacture of a medicament for the treatment of cancer, wherein the medicament also comprises one or more chemotherapy agents or is to be administered simultaneously, separately or sequentially with one or more chemotherapy agents.

The present invention provides use of 5-(5-(2-(3-aminopropoxy)-6-methoxyphenyl)-1H-pyrazol-3-ylamino)pyrazine-2-carbonitrile (S)-lactate monohydrate for the manufacture of a medicament for the treatment of cancer, wherein the medicament is to be administered simultaneously, separately or sequentially with ionizing radiation and one or more chemotherapy agents.

The present invention provides 5-(5-(2-(3-aminopropoxy)-6-methoxyphenyl)-1H-pyrazol-3-ylamino)pyrazine-2-carbonitrile (S)-lactate monohydrate for use in simultaneous, separate or sequential combination with ionizing radiation in the treatment of cancer.

The present invention provides 5-(5-(2-(3-aminopropoxy)-6-methoxyphenyl)-1H-pyrazol-3-ylamino)pyrazine-2-carbonitrile (S)-lactate monohydrate for use in simultaneous, separate or sequential combination with one or more chemotherapy agents in the treatment of cancer.

The present invention provides 5-(5-(2-(3-aminopropoxy)-6-methoxyphenyl)-1H-pyrazol-3-ylamino)pyrazine-2-carbonitrile (S)-lactate monohydrate for use in simultaneous, separate or sequential combination with one or more chemotherapy agents and ionizing radiation in the treatment of cancer.

The present invention provides a pharmaceutical composition comprising 5-(5-(2-(3-aminopropoxy)-6-methoxyphenyl)-1H-pyrazol-3-ylamino)pyrazine-2-carbonitrile (S)-lactate monohydrate together with a pharmaceutically acceptable carrier and optionally other therapeutic ingredients.

Furthermore, the present invention provides preferred embodiments of the methods and uses as described herein, in which the chemotherapy agent is selected from the group consisting of 5-fluorouracil, hydroxyurea, gemcitabine, methotrexate, pemetrexed, cetuximab, doxorubicin, etoposide, cisplatin, taxol, and combinations thereof.

Preferred embodiments of the methods and uses described herein are cancers selected from the group consisting of bladder cancer, colon cancer, gastric cancer, liver cancer, lung cancer, mammary cancer, melanoma, ovarian cancer, pancreatic cancer, mesothelioma, renal cancer, anal cancer, head and neck cancer, small cell lung cancer, and uterine cancer.

5-(5-(2-(3-aminopropoxy)-6-methoxyphenyl)-1H-pyrazol-3-ylamino)pyrazine-2-carbonitrile (S)-lactate monohydrate may exist as tautomeric forms. When tautomeric forms exist, each form and mixtures thereof, are contemplated in the present invention.

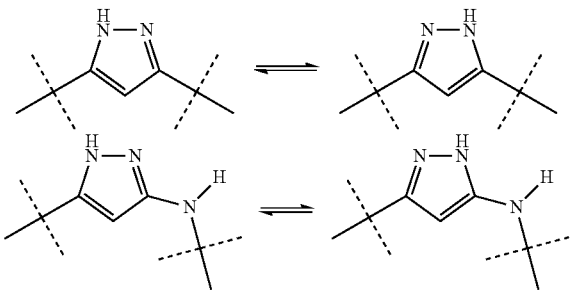

As used herein, the term "patient" refers to a human or nonhuman mammal. More particularly, the term "patient" refers to a human.

The term "treating" (or "treat" or "treatment") refers to the process involving a slowing, interrupting, arresting, controlling, reducing, or reversing the progression or severity of a symptom, disorder, condition, or disease.

As used herein, the term "effective amount" refers to the amount or dose of the compound of the present invention, described herein, alone or in combination with ionizing radiation or a chemotherapy agent which, upon single or multiple dose administration to the patient, provides the desired effect in the patient under diagnosis or treatment. An effective amount can be readily determined by the attending diagnostician, as one skilled in the art, by considering a number of factors such as the species of mammal; its size, age, and general health; the co-administration of other agents, if needed; the specific disease involved; the degree or severity of the disease; the response of the individual patient; the particular compound administered; the mode of administration; the bioavailability characteristics of the preparation administered; the dose regimen selected; the use of any concomitant medications; and other relevant circumstances. While not to be construed as limiting the present invention in any way, 20-150 mg/m$^2$ represents an effective amount of the compound described herein.

As used herein, the term "combination therapy" refers to: separate, simultaneous, or sequential administration of the compound of the present invention and chemotherapy agent(s); separate, simultaneous, or sequential administration of the compound of the present invention and ionizing radiation; and separate, simultaneous, or sequential administration of the compound of the present invention, one or more chemotherapy agents, and ionizing radiation.

The 5-(5-(2-(3-aminopropoxy)-6-methoxyphenyl)-1H-pyrazol-3-ylamino)pyrazine-2-carbonitrile (S)-lactate monohydrate may be formulated for administration as part of a pharmaceutical composition. As such, pharmaceutical compositions can comprise 5-(5-(2-(3-aminopropoxy)-6-methoxyphenyl)-1H-pyrazol-3-ylamino)pyrazine-2-carbonitrile (S)-lactate monohydrate and one or more of the following: pharmaceutically acceptable carriers, excipients, and diluents. Examples of pharmaceutical compositions and methods for their preparation are well known in the art. (See, e.g., REMINGTON: THE SCIENCE AND PRACTICE OF PHARMACY, A. Gennaro, et al., eds., 22$^{nd}$ ed., Pharmaceutical Press (2012).)

The 5-(5-(2-(3-aminopropoxy)-6-methoxyphenyl)-1H-pyrazol-3-ylamino)pyrazine-2-carbonitrile (S)-lactate monohydrate can be administered by any route which makes it bioavailable, including oral and parenteral routes. For example, 5-(5-(2-(3-aminopropoxy)-6-methoxyphenyl)-1H-pyrazol-3-ylamino)pyrazine-2-carbonitrile (S)-lactate monohydrate can be administered orally, subcutaneously, intramuscularly, intravenously, transdermally, topically, intranasally, rectally, buccally, and the like. Alternatively, 5-(5-(2-(3-aminopropoxy)-6-methoxyphenyl)-1H-pyrazol-3-ylamino)pyrazine-2-carbonitrile (S)-lactate monohydrate can be administered by infusion. IV infusion is the preferred route of administration.

The reactions described herein may be performed via standard techniques known to the skilled artisan by employing routine glassware, but also by using autoclave pressure chambers. These reactions also may be performed at a pilot and/or production scale using equipment designed for such transformations. Further, each of these reactions described may be executed via a batch process, flow reaction methodology, or as described herein. "Batch process" means a process in which raw materials are combined in a reactor or vessel and product is removed at the end of the reaction. "Continuous processing" or "flow reaction" refers to a process in which there is a continuous inflow of raw materials and outflow of product. Such continuous processing enables a platform where the final product may be synthesized by a fully continuous train of operations starting from initial starting materials. In some examples, the production of the final product may be synthesized using a combination of batch and flow processing.

Certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See, e.g., "*Greene's Protective Groups in Organic Synthesis*", Fifth Edition, by Peter G. M. Wuts, John Wiley and Sons, Inc. 2014.)

One of ordinary skill in the art will recognize that 5-(5-(2-(3-aminopropoxy)-6-methoxyphenyl)-1H-pyrazol-3-ylamino)pyrazine-2-carbonitrile methanesulfonic acid monohydrate can alternatively be referred to as 2-pyrazinecarbonitrile, 5-[[5-[2-(3-aminopropoxy)-6-methoxyphenyl]-1H-pyrazol-3-yl]amino]monomesylate monohydrate.

Individual isomers, enantiomers, and diastereomers may be separated or resolved by one of ordinary skill in the art at any convenient point in the synthesis of compounds of the invention, by methods such as selective crystallization techniques or chiral chromatography (See, e.g., J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994.)

Certain abbreviations are defined as follows: "DMF" refers to dimethylformamide; "DMSO" refers to dimethyl sulfoxide; "eqv" refers to equivalent; "HPLC" refers to high performance liquid chromatography; "K$_3$EDTA" refers to potassium ethylenediaminetetraacetic acid; "methanesulfonic acid" refers to mesylate or monomesylate; "MTBE" refers to methyl-tert-butyl ether; "n-PrOH" refers to n-propanol or n-propyl alcohol; "PTFE" refers to polytetrafluoroethylene; "PVDE" refers to polyvinylidene fluoride; "Q" refers to flow rate; "q.s." refers to quantum sufficit; "RP" refers to reverse phase; "(S)-lactate" refers to (L)-lactate or (2S)-2-hydroxypropanoic acid; "τ" is residence time or the average amount of time a discrete quantity of reagent spends inside the tank; "TFA" refers to trifluoroacetic acid; "THF" refers to tetrahydrofuran; "V" refers to the volume of the reactor; and "XPRD" refers to X-ray powder diffraction.

The compounds of the present invention may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention. The products can be recovered by conventional methods well known in the art, including extraction, evaporation, precipitation, chromatography, filtration, trituration, and crystallization. The reagents and starting materials are readily available to one of ordinary skill in the art. The following schemes, preparations, and examples further illustrate the invention.

Batch Processing Scheme 1

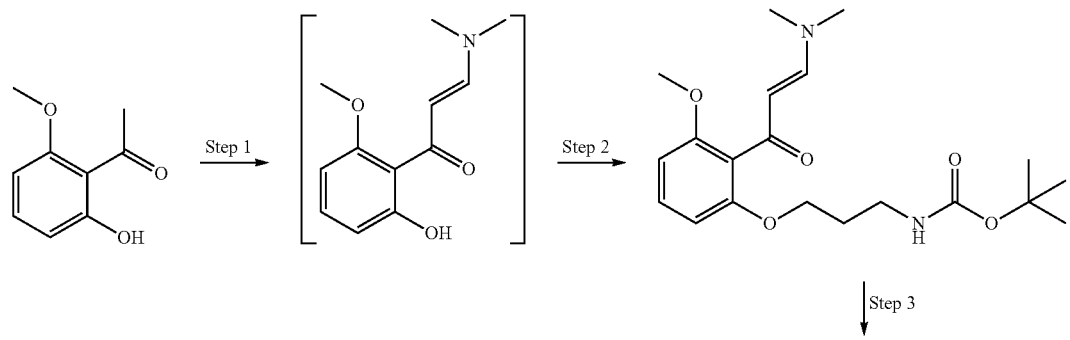

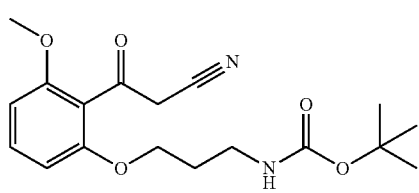
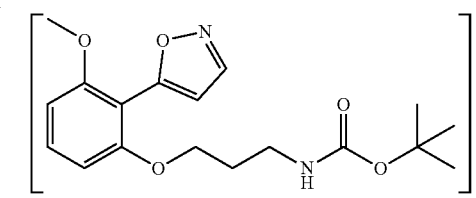
-continued
Step 4
Continuous Flow Processing Scheme 2
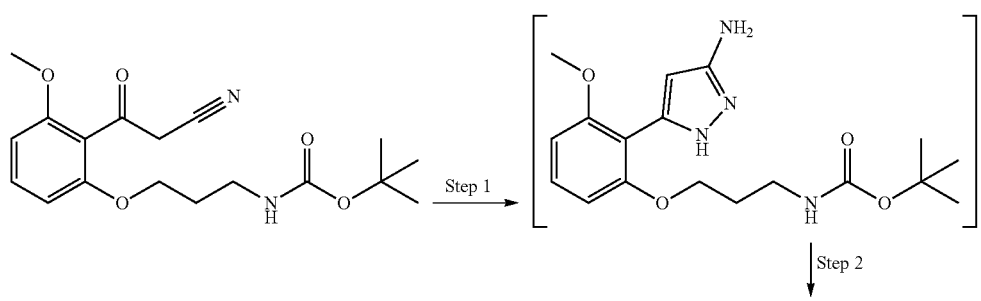
Step 1
Step 2
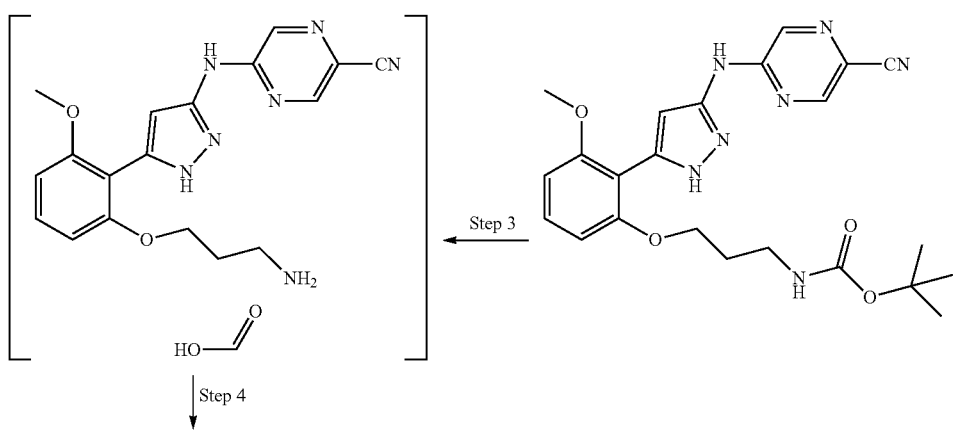
Step 3
Step 4
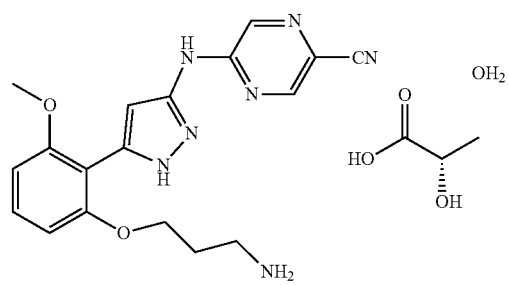

Preparation 1 tert-Butyl (E)-(3-(2-(3-(dimethylamino)acryloyl)-3-methoxyphenoxy)propyl)carbamate

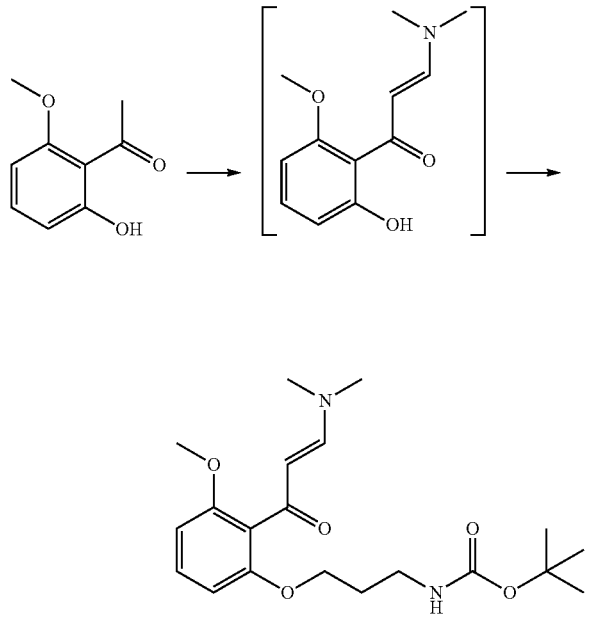

Combine 1-(2-hydroxy-6-methoxyphenyl)ethan-1-one (79.6 kg, 479 mol) and 1,1-dimethoxy-N,N-dimethylmethanamino (71.7 kg, 603.54 mol) with DMF (126 kg). Heat to 85-90° C. for 12 hours. Cool the reaction mixture containing intermediate (E)-3-(dimethylamino)-1-(2-hydroxy-6-methoxyphenyl)prop-2-en-1-one (mp 84.74° C.) to ambient temperature and add anhydrous potassium phosphate (136 kg, 637.07 mol) and tert-butyl (3-bromopropyl)carbamate (145 kg, 608.33 mol). Stir the reaction for 15 hours at ambient temperature. Filter the mixture and wash the filter cake with MTBE (3×, 433 kg, 300 kg, and 350 kg). Add water (136 kg) and aqueous sodium chloride (25% solution, 552 kg) to the combined MTBE organic solutions. Separate the organic and aqueous phases. Back-extract the resulting aqueous phase with MTBE (309 kg) and add the MTBE layer to the organic solution. Add an aqueous sodium chloride solution (25% solution, 660 kg) to the combined organic extracts and separate the layers. Concentrate the organic extracts to 1,040 kg-1,200 kg and add water (400 kg) at 30-35° C. to the residue. Cool to ambient temperature and collect material by filtration as a wet cake to give the title product (228.35 kg, 90%). ES/MS (m/z): 379.22275 (M+1).

Preparation 2 tert-Butyl (3-(2-(2-cyanoacetyl)-3-methoxyphenoxy)propyl)carbamate

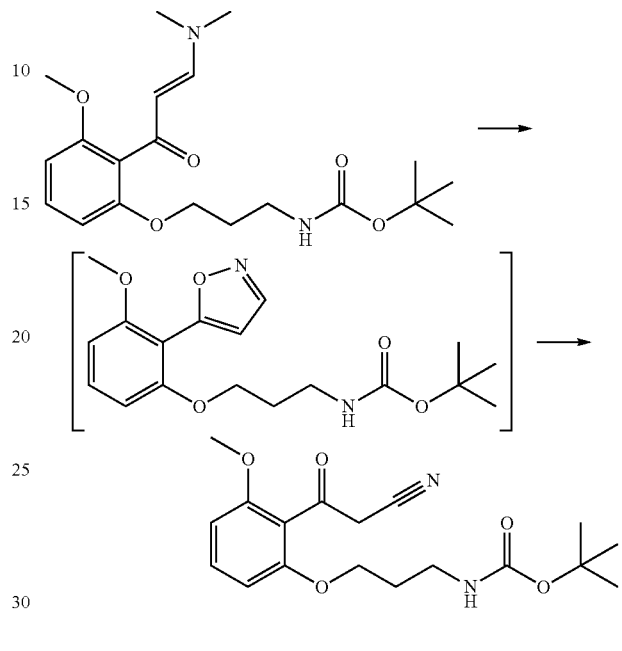

Combine ethanol (1044 kg), hydroxyl amino hydrochloride (30 kg, 431.7 mol), and tert-butyl (E)-(3-(2-(3-(dimethylamino)acryloyl)-3-methoxyphenoxy)propyl)carbamate (228.35 kg, 72% as a wet water solid, 434.9 mol) to form a solution. Heat the solution to 35-40° C. for 4-6 hours. Cool the reaction to ambient temperature and concentrate to a residue. Add MTBE (300 kg) to the residue and concentrate the solution to 160 kg-240 kg. Add MTBE (270 kg) and concentrate the solution. Add MTBE (630 kg), water (358 kg), and sodium chloride solution (80 kg, 25% aqueous) and stir for 20 minutes at ambient temperature. Let the mixture stand for 30 minutes. Separate the aqueous layer. Add water (360 kg) and sodium chloride solution (82 kg, 25% sodium chloride) to the organic phase. Stir for 20 minutes at ambient temperature. Let the mixture stand for 30 minutes. Separate the aqueous portion. Add sodium chloride solution (400 kg, 25% aqueous) to the organic portion. Stir for 20 minutes at ambient temperature. Let the mixture stand for 30 minutes at ambient temperature. Separate the aqueous portion. Concentrate the organic portion to 160 kg-240 kg at 40° C. Add ethanol (296 kg) to the organic portion. Concentrate the solution to 160 kg to 240 kg at 40° C. to provide an intermediate of tert-butyl (3-(2-(isoxazol-5-yl)-3-methoxyphenoxy)propyl)carbamate. Add ethanol (143 kg) and water (160 kg) to the concentrated solution. Add potassium hydroxide (31.8 kg) at 40° C. Add ethanol (80 kg) and adjust the temperature to 45-50° C. Stir for 4-6 hours at 45-50° C. and concentrate to 160 kg-240 kg at 40° C. Add water to the concentrate (160 kg) and acetic acid (9.0 kg) drop-wise to adjust the pH to 10-12 while maintaining the temperature of the solution at 25 to 35° C. Add ethyl acetate (771 kg) and acetic acid drop-wise to adjust the pH to 5-7 while maintaining the temperature of the solution at 25-35° C. Add sodium chloride solution (118 kg, 25% aqueous solution). Stir the mixture for 20 minutes at ambient temperature. Let the solution stand for 30 minutes at ambient temperature. Separate the aqueous portion. Heat the organic portion to 30-35° C. Add water (358 kg) drop-wise. Stir the solution for 20 minutes while maintaining the temperature at 30 to 35° C. Let the mixture stand for 30 minutes and separate the aqueous portion. Wash the organic portion with sodium chloride solution (588 kg, 25% aqueous) and concentrate the organic portion to 400 kg-480 kg at 40-50° C. Heat the concentrated solution to 50° C. to form a solution. Maintain the solution at 50° C. and add n-heptane (469 kg) drop-wise. Stir the solution for 3 hours at 50° C. before slowly cooling to ambient temperature to crystallize the product. Stir at ambient temperature for 15 hours and filter the crystals. Wash the crystals with ethanol/n-heptane (1:2, 250 kg) and dry at 45° C. for 24 hours to provide the title compound (133.4 kg, 79.9%), m.p. 104.22° C.

EXAMPLE 1

5-(5-(2-(3-Aminopropoxy)-6-methoxyphenyl)-1H-pyrazol-3-ylamino)pyrazine-2-carbonitrile (S)-lactate Monohydrate

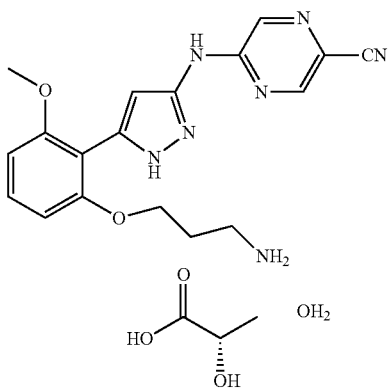

Combine a THF solution (22%) of tert-butyl (3-(2-(2-cyanoacetyl)-3-methoxyphenoxy)propyl)carbamate (1.0 eqv, this is define as one volume) with hydrazine (35%, 1.5 eqv), acetic acid (glacial, 1.0 eqv), water (1 volume based on the THF solution) and methanol (2 volumes based on the THF solution). This is a continuous operation. Heat the resulting mixture to 130° C. and 1379 kPa with a rate of V/Q=70 minutes, tau=60. Extract the solution with toluene (4 volumes), water (1 volume), and sodium carbonate (10% aqueous, 1 eqv). Isolate the toluene layer and add to DMSO (0.5 volumes). Collect a solution of the intermediate compound tert-butyl (3-(2-(3-amino-1H-pyrazol-5-yl)-3-methoxyphenoxy) propyl)carbamate (26.59 kg, 91%) in 10 days, mp=247.17° C. as a DMSO solution (3 volumes of product). N-Ethylmorpholine (1.2 eqv) and 5-chloropyrazine-2-carbonitrile (1.15 eqv) in 2 volumes of DMSO is combined in a tube reactor at 80° C., V/Q=3 and tau=170 minutes at ambient pressure. Add the product stream to methanol (20 vol). As a continuous process, filter the mixture and wash with methanol followed by MTBE. Air dry the material on the filter to give tert-butyl (3-(2-(3-((5-cyanopyrazin-2-yl)amino)-1H-pyrazol-5-yl)-3-methoxyphenoxy) propyl)carbamate in a continuous fashion (22.2 kg, 88.7%, 8 days). Dissolve a solution of tert-butyl (3-(2-(3-((5-cyanopyrazin-2-yl)amino)-1H-pyrazol-5-yl)-3-methoxyphenoxy) propyl)carbamate in formic acid (99%, 142 kg) at ambient temperature and agitate for 4 hours to provide an intermediate of 5-((5-(2-(3-aminopropoxy)-6-methoxyphenyl)-1H-pyrazol-3-yl)amino)pyrazine-2-carbonitrile formate. Dilute the solution with water (55 kg), (S)-lactic acid (30%, 176 kg) and distill the resulting mixture until <22 kg formic acid remains. Crystallize the resulting residue from THF and wash with a THF-water (0.5% in THF) solution. Dry the wet cake at 30° C. at >10% relative humidity to give the title product as a white to yellow solid (24.04 kg, 85-90%), m.p. 157° C.

ALTERNATE PREPARATION EXAMPLE 1

5-(5-(2-(3-Aminopropoxy)-6-methoxyphenyl)-1H-pyrazol-3-ylamino)pyrazine-2-carbonitrile (S)-lactate Monohydrate Add 5-({3-[2-(3-aminopropoxy)-6-methoxyphenyl]-1H-pyrazol-5-yl}amino)pyrazine-2-carbonitrile (4.984 g, 13.33 mmol, 97.7 wt %) to n-PrOH (15.41 g, 19.21 mL) to form a slurry. Heat the slurry to 60° C. Add (S)-lactic acid (1.329 g, 14.75 mmol) to water (19.744 mL) and add this solution to the slurry at 58° C. Heat the solution to 60° C. and add n-PrOH (21.07 g, 26.27 mL). Seed the solution with 5-((5-(2-(3-aminopropoxy)-6-methoxyphenyl)-1H-pyrazol-3-yl)amino)pyrazine-2-carbonitrile (S)-lactate monohydrate (48.8 mg, 0.1 mmol) and cool the solution to 40° C. over 35 minutes. Add n-PrOH (60.5 mL) to the slurry at 40° C. via a syringe pump over 2 hours and maintain the temperature at 40° C. Once complete, air cool the slurry to ambient temperature for 2 hours, the cool the mixture in ice-water for 2 hours. Filter the product, wash the wet cake with 6:1 (v/v) n-PrOH:H₂O (15 mL), followed by n-PrOH (15 mL) and dry the wet cake for 20 minutes. Dry the solid overnight at 40° C. in vacuo to give the title compound as a white to yellow solid (5.621 g, 89.1%), m.p. 157° C.

CRYSTALLINE EXAMPLE 1

Crystalline 5-(5-(2-(3-aminopropoxy)-6-methoxyphenyl)-1H-pyrazol-3-ylamino)pyrazine-2-carbonitrile (S)-lactate Monohydrate Prepare a slurry having 5-(5-(2-(3-aminopropoxy)-6-methoxyphenyl)-1H-pyrazol-3-ylamino)pyrazine-2-carbonitrile (368 mg, 1.0 mmol) in a 10:1 THF-water (5 mL) solution and stir at 55° C. Add (S)-lactic acid (110 mg, 1.22 mmol) dissolved in THF (1 mL). A clear solution forms. Stir for one hour. Reduce the temperature to 44° C. and stir until an off-white precipitate forms. Filter the material under vacuum, rinse with THF, and air dry to give the title compound (296 mg, 80%).

X-RAY POWDER DIFFRACTION, CRYSTALLINE EXAMPLE 1

Obtain the XRPD patterns of the crystalline solids on a Bruker D4 Endeavor X-ray powder diffractometer, equipped with a CuKa source (λ=1.54060 Å) and a Vantec detector, operating at 35 kV and 50 mA. Scan the sample between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. Pack the dry powder on a quartz sample holder and obtain a smooth surface using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 35—National Formulary 30 Chapter <941> Characterization of crystalline and partially crystalline solids by XRPD Official Dec. 1, 2012-May 1, 2013. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, were adjusted based on NIST 675 standard peaks at 8.85 and 26.77 degrees 2-theta.

Characterize a prepared sample of crystalline 5-(5-(2-(3-aminopropoxy)-6-methoxyphenyl)-1H-pyrazol-3-ylamino) pyrazine-2-carbonitrile (S)-lactate monohydrate by an XPRD pattern using CuKa radiation as having diffraction peaks (2-theta values) as described in Table 1 below. Specifically the pattern contains a peak at 12.6 in combination with one or more of the peaks selected from the group consisting of 24.8, 25.5, 8.1, 6.6, 12.3, and 16.3 with a tolerance for the diffraction angles of 0.2 degrees.

X-RAY POWDER DIFFRACTION PEAKS OF CRYSTALLINE EXAMPLE 1

TABLE 1

| Peak | Angle (2-Theta) +/− 0.2° | Relative Intensity (% of most intense peak) |
|---|---|---|
| 1 | 6.6 | 58 |
| 2 | 8.1 | 63 |
| 3 | 12.3 | 61 |
| 4 | 12.6 | 100 |
| 5 | 16.3 | 57 |
| 6 | 20.9 | 34 |
| 7 | 21.1 | 49 |
| 8 | 24.8 | 87 |
| 9 | 25.1 | 31 |
| 10 | 25.5 | 78 |

Formulation of 5-(5-(2-(3-aminopropoxy)-6-methoxyphenyl)-1H-pyrazol-3-ylamino)pyrazine-2-carbonitrile (S)-lactate Monohydrate Add warm water (2500 mL, 35-40° C.) and 5-((5-(2-(3-aminopropoxy)-6-methoxyphenyl)-1H-pyrazol-3-yl)amino) pyrazine-2-carbonitrile (S) lactate monohydrate (22.208 g, 46.9 mmol) to a manufacturing vessel with stirring. Stir for 10 minutes until the material dissolves and yields a clear solution. Add trehalose dihydrate (26.28 g, 69.46 mmol), mannitol (146.92 g, 806.49 mmol), and polysorbate 80 (6.528 g, 4.98 mmol) to the manufacturing vessel. Stir until dissolved. Add water (788.29 mL) to bring the solution to the final batch weight (3288.29 mL). Filter the solution through a sterile 0.22 micron PVDF membrane (Millipore Durapore®) into a clean, dry receiving vessel. Fill the drug product solution into sterile vials (20.6 mL fill into 50 mL vial; total vials: 144 including 5 thermocouple vials). Upon completion of filling, partially stopper the vials and place into the lyophilizer Upon completion of the lyophilization cycle (4 days), fully stopper the vials under a slight vacuum (662 mbar) and seal. Store all vials at room temperature (15-25° C.).

Alternate Formulation of 5-(5-(2-(3-aminopropoxy)-6-methoxyphenyl)-1H-pyrazol-3-ylamino)pyrazine-2-carbonitrile (S)-lactate Monohydrate Add Water for Injection, (WFI) at room temperature (4000 mL) to a manufacture vessel. Add polysorbate 80 (6.25 g, 4.77 mmol) with stirring. Stir until the material dissolves and yields a clear solution. Add mannitol (150.0 g, 823.4 mmol) and stir until visually clear. Add trehalose dihydrate (129.86 g, 343.2 mmol) and then stir until visually clear. Add 1 N lactic acid (3.25 mL per L of batch solution) to the manufacturing vessel and stir until visually clear. Add 5-((5-(2-(3-aminopropoxy)-6-methoxyphenyl)-1H-pyrazol-3-yl)amino)pyrazine-2-carbonitrile (S) lactate monohydrate (21.71 g, 45.8 mmol) to the manufacturing vessel and stir until dissolved. Add WFI to bring the solution to the final batch volume (5000 mL). Filter the solution through a sterile 0.22 micron PVDF membrane (Millipore Durapore®) into a clean, dry receiving vessel. Fill the drug product solution into sterile vials (20.6 mL fill into 50 mL vial). Upon completion of filling, partially stopper the vials and place into the lyophilizer. Upon completion of the lyophilization cycle (3-4 days), fully stopper the vials under a slight vacuum (about 866 mbar) and seal. Store all vials at refrigerated conditions (2-8° C.).

Salt Selection

General Method for Solubility Screen of 5-(5-(2-(3-aminopropoxy)-6-methoxyphenyl)-1H-pyrazol-3-ylamino)pyrazine-2-carbonitrile HCl, Methanesulfonic Acid Monohydrate and (S)-Lactate Monohydrate Salts Prepare an aqueous solution (approximately 0.1 M) of selected acid. Add solid 5-(5-(2-(3-aminopropoxy)-6-methoxyphenyl)-1H-pyrazol-3-ylamino)pyrazine-2-carbonitrile (20-26 mg). Agitate slurry at room temperature for one week. Measure the 5-(5-(2-(3-aminopropoxy)-6-methoxyphenyl)-1H-pyrazol-3-ylamino)pyrazine-2-carbonitrile concentration by HPLC. Aliquots (~200 µL) are withdrawn from the suspensions through 0.45 micron Millex® PTFE filters. Dilute samples with mobile phase and analyze by HPLC. Analyze the samples with an Agilent 1100 HPLC (Instrument 800) with a Zorbax Bonus RP (75 mm×4.6 mm, 3.5 micron particle size) column, or equivalent. The mobile phase consists of 20% of a 0.1% TFA in acetonitrile mixture and 80% of a 0.1% TFA in water mixture. Instrument conditions are as follows: flow rate 1.0 mL/minute, wavelength of detection 290 nm, 3 µL injection volume, 10 minute run time, and column temperature of 30° C. Prepare a stock solution of 5-(5-(2-(3-aminopropoxy)-6-methoxyphenyl)-1H-pyrazol-3-ylamino)pyrazine-2-carbonitrile in 50/50 water/acetonitrile and dilute with 50/50 water/acetonitrile to give concentrations suitable for quantification of the solubility samples. Dilute the samples with 50/50 acetonitrile/water. Use a dilution factor of 200 for the samples. Measure the pH of each solution and analyze the solid residues by microscopy and XRPD (wet and dry) for crystallinity and crystal form.

Comparison of the Di-HCl, Methanesulfonic Acid Monohydrate, and (S)-lactate Monohydrate Salts of 5-(5-(2-(3-aminopropoxy)-6-methoxyphenyl)-1H-pyrazol-3-ylamino)pyrazine-2-carbonitrile

TABLE 2

| Parameters | Di-HCl | Methanesulfonic acid Monohydrate | (S)-Lactate Monohydrate |
|---|---|---|---|
| Solubility (mg/mL) | 0.107 | 6.63 | >20 |
| Captisol ® Required | Yes | Yes | No |
| Cost of Manufacturing | Very high | High | Low |
| Lyophilization Cycle (Time) | N.D.[1] | 9.5 days | 3-4 days |
| # of vials required for 210 mg dose | >11[2] | 11[2] | 4[2] |
| Stability | Unstable | Satisfactory | Satisfactory |

[1]N.D. means not determined.
[2]For comparison purposes, use 20 mL vials.

Table 2 illustrates the parameters that describe di-HCl, methanesulfonic acid monohydrate, and (S)-lactate monohydrate salts of 5-(5-(2-(3-aminopropoxy)-6-methoxyphenyl)-1H-pyrazol-3-ylamino)pyrazine-2-carbonitrile. The parameters are solubility, stability, lypholization cycle time, Captisol® which is a form of cyclodextrin that aids in solubility, relative manufacturing cost, and the number of IV vials required for the administration of an exemplary dose for the formulated drug. The solubility of 5-(5-(2-(3-aminopropoxy)-6-methoxyphenyl)-1H-pyrazol-3-ylamino)pyrazine-2-carbonitrile (S)-lactate monohydrate has a >20 mg/mL solubility in water when measured at a pH of 2.46. The solubility of 5-(5-(2-(3-aminopropoxy)-6-methoxyphenyl)-1H-pyrazol-3-ylamino)pyrazine-2-carbonitrile methanesulfonic acid monohydrate salt solubility is 6.63 mg/mL and the solubility of 5-(5-(2-(3-aminopropoxy)-6-methoxyphenyl)-1H-pyrazol-3-ylamino)pyrazine-2-carbonitrile di-HCl salt solubility is 0.107 mg/mL. Therefore the solubility of the (S)-lactate monohydrate salt is superior to the di-HCl and methanesulfonic acid monohydrate salts in a water solubility comparison. Furthermore, because of the very low solubility, the di-HCl salt form is not advantageous for formulation of the final product.

The (S)-lactate monohydrate form also requires a lower lyophilization cycle time than the methanesulfonic acid monohydrate salt. The methanesulfonic acid monohydrate salt has a lyophilization cycle of 9.5 days whereas the (S)-lactate monohydrate formulation has a lyophilization time of 3-4 days. This cycle time means that product containing the methanesulfonic acid monohydrate formulation is in the freeze dryer for more than twice the time as compared to the (S)-lactate monohydrate formulation, increasing the potential for system failure during the extended processing time period (e.g., equipment failures, sterility breach, etc.) that may require the batch to be discarded.

Furthermore, the (S)-lactate monohydrate salt does not require Captisol®, a relatively expensive solubilization aid. As a result, the (S)-lactate monohydrate salt is less expensive to formulate as compared to the di-HCl and methanesulfonic acid monohydrate salt forms.

Solubility Screen

Crystalline 5-(5-(2-(3-Aminopropoxy)-6-methoxyphenyl)-1H-pyrazol-3-ylamino)pyrazine-2-carbonitrile (S)-lactate Monohydrate Prepare a (S)-lactic acid aqueous solution (0.104 M, 1 mL). Add solid 5-(5-(2-(3-aminopropoxy)-6-methoxyphenyl)-1H-pyrazol-3-ylamino)pyrazine-2-carbonitrile (21.7 mg, 0.059 mmol). Agitate the slurry at room temperature for one week. Measure the 5-(5-(2-(3-aminopropoxy)-6-methoxyphenyl)-1H-pyrazol-3-ylamino)pyrazine-2-carbonitrile concentration by HPLC. Withdraw an aliquot (~200 µL) from the suspension through 0.45 micron Millex® PTFE filters. Dilute the samples with mobile phase and analyze by HPLC. Analyze the samples with an Agilent 1100 HPLC (Instrument 800) with a Zorbax Bonus RP (75 mm×4.6 mm, 3.5 micron particle size) column, or equivalent. The mobile phase consists of 20% of a 0.1% TFA in acetonitrile mixture and 80% of a 0.1% TFA in water mixture. Instrument conditions are as follows: flow rate 1.0 mL/minute, wavelength of detection 290 nm, 3 µL injection volume, 10 minute run time, and column temperature of 30° C. Prepare a stock solution of 5-(5-(2-(3-aminopropoxy)-6-methoxyphenyl)-1H-pyrazol-3-ylamino)pyrazine-2-carbonitrile in 50/50 water/acetonitrile and dilute with 50/50 water/acetonitrile to give concentrations suitable for quantification of the solubility samples. Dilute the samples with 50/50 acetonitrile/water. Use a dilution factor of 200 for the samples. The solubility of 5-(5-(2-(3-aminopropoxy)-6-methoxyphenyl)-1H-pyrazol-3-ylamino)pyrazine-2-carbonitrile (S)-lactate monohydrate is >20 mg/mL at a pH of 2.46.

Pharmacokinetic Comparison of the Methanesulfonic Acid Monohydrate and (S)-lactate Monohydrate Salts of 5-(5-(2-(3-aminopropoxy)-6-methoxyphenyl)-1H-pyrazol-3-ylamino)pyrazine-2-carbonitrile Evaluate the noncompartmental pharmacokinetic parameters of the methanesulfonic acid monohydrate and (S)-lactate monohydrate salts of 5-(5-(2-(3-aminopropoxy)-6-methoxyphenyl)-1H-pyrazol-3-ylamino)pyrazine-2-carbonitrile after intravenous (IV) infusion of 10 mg/kg of the methanesulfonic acid monohydrate salt (10 mg/kg, formulated in Captisol®) or of the (S)-lactate monohydrate salt (formulated in trehalose) into the femoral vein cannula of fed male Sprague-Dawley rats for 1 hour. Collect blood samples over 24 hours from 6 animals/group. Collect blood samples into tubes containing $K_3EDTA$ at 0.25, 0.5, 1, 1.25, 1.5, 2, 4, 8, and 24 hours after the start of infusion. Centrifuge the samples to obtain plasma, and freeze until analyzed. Determine plasma concentrations using a validated LC-MS/MS assay. Statistical analysis of this data using a 2 sample t-test (pooled error) showed that no significant difference is observed with respect to blood plasma levels of either salt form after IV injection.

Preparation of 5-(5-(2-(3-aminopropoxy)-6-methoxyphenyl)-1H-pyrazol-3-ylamino)pyrazine-2-carbonitrile (S)-lactacte Monohydrate Salt for IV Injection Dispense WFI equivalent to approximately 80% of the final batch volume. Warm the WFI to 40° C.±3° C. and transfer to the manufacturing vessel. Weigh the required amount of active pharmaceutical ingredient and after ensuring that the WFI temperature is still within the specified range, quantitatively transfer the active pharmaceutical ingredient into the manufacturing vessel while stirring. Stir until the active pharmaceutical ingredient has dissolved yielding a clear yellow solution, stirring for no longer than 30 minutes. Add trehalose and polysorbate 80 to the manufacturing vessel. Stir until dissolved. Measure the pH of the solution and adjust to pH 4.4±0.3 with lactic acid (Note: If using lactic acid 88%-92% solution, titrate slowly and cautiously as small quantities can produce large changes in pH, or prepare a 10% solution of lactic acid for pH adjustment). If necessary, and only if the pH drops below the lower limit during adjustment, add 10% NaOH solution to bring the pH back into range. Add WFI to the manufacturing vessel to bring the solution to the final batch weight which is calculated based on the desired batch volume and the density of the solution. Measure the pH of the solution and adjust, if necessary, to pH 4.4±0.3 with lactic acid or 10% NaOH. The solution is filtered through a sterile 0.22 micron PVDF membrane (Millipore Durapore®) into a sterile receiving vessel. Fill the drug product into sterile vials. Upon completion of filling, stopper and seal vials. If not dosed within about 4 hours, store all vials at −20° C. The unit formula is shown in Table 3.

TABLE 3

| Unit Formula Active Ingredient | Quantity (mg/mL) |
|---|---|
| (S)-lactate monohydrate[1] salt | 2.59 (Equivalent to 2.0 free base) |
| Other Ingredients[2] | |
| Trehalose | 14.74 |
| Polysorbate 80 | 0.76 |
| Water for Injection | q.s. |
| Lactic Acid or Sodium hydroxide solution[3] | — |

[1]The amount of active pharmaceutical ingredient may be adjusted to take into account the Assay "as is, free base" of the drug substance. Assay "as is, free base" can be defined as the portion of the drug substance (fraction or a percentage on a mass basis) that is comprised of the active moiety, as measured by an appropriate analytical chemistry technique and that is not corrected for the presence of volatile substances.
[2]A reasonable variation of +/−10% is allowed for each excipient unless otherwise stated.
[3]Quantity sufficient to adjust pH.

Alternate Preparation of 5-(5-(2-(3-aminopropoxy)-6-methoxyphenyl)-1H-pyrazol-3-ylamino)pyrazine-2-carbonitrile (S)-lactacte Monohydrate Salt for IV Injection Dispense WFI equivalent to approximately 80% of the final batch volume. Weigh the required amount of polysorbate 80 and add to the vessel while stirring until visually clear. Weigh the required amount of mannitol and add to the vessel while stirring until visually clear. Weigh the required amount of trehalose dihydrate and add to the vessel while stirring until visually clear. Add the appropriate amount of lactic acid to the vessel while stirring until visually clear. Weigh the required amount of active pharmaceutical ingredient and transfer the active pharmaceutical ingredient into the manufacturing vessel while stirring. Stir until the active pharmaceutical ingredient has dissolved yielding a clear yellow solution. Measure the pH of the solution and adjust to pH 4.2±0.3 with lactic acid (Note: If using lactic acid 88%-92% solution, titrate slowly and cautiously as small quantities can produce large changes in pH, or prepare a 10% solution of lactic acid for pH adjustment). Add WFI to the manufacturing vessel to bring the solution to the final batch weight which is calculated based on the desired batch volume and the density of the solution. The pH of the solution is measured and adjusted, if necessary, to pH 4.2±0.3 with lactic acid. The solution is filtered through a sterile 0.22 micron PVDF membrane (Millipore Durapore®) into a sterile receiving vessel. Fill the drug product into sterile vials. Upon completion of filling, partially stopper the vials and place the vials into the lyophilizer. Upon completion of the lyophilization cycle (about 3-4 days), fully stopper the vials under a slight vacuum (target 866 mbar) and seal. Store all vials at refrigerated conditions (2-8° C.). The unit formula is shown in Table 4.

TABLE 4

| Unit Formula Active Ingredient | Quantity (mg/mL) |
|---|---|
| (S)-lactate monohydrate[1] salt | 4.34 (Equivalent to 3.35 free base) |
| Other Ingredients[2] | |
| Trehalose | 23.5 |
| Mannitol | 30.0 |
| Polysorbate 80 | 1.25 |
| Water for Injection | q.s. |
| Lactic Acid or Sodium hydroxide solution[3] | — |

[1]The amount of active pharmaceutical ingredient may be adjusted to take into account the Assay "as is, free base" of the drug substance.
[2]A reasonable variation of +/−10% is allowed for each excipient unless otherwise stated.
[3]Quantity sufficient to adjust pH.

Alternate Preparation of 5-(5-(2-(3-aminopropoxy)-6-methoxyphenyl)-1H-pyrazol-3-ylamino)pyrazine-2-carbonitrile Methanesulfonic Acid Monohydrate Salt for IV Injection Dispense WFI equivalent to approximately 80% of the final batch volume into the manufacturing vessel. Weigh the required amount of Captisol® and transfer to the manufacturing vessel. Stir until dissolved. Weigh the required amount of active pharmaceutical ingredient and form a slurry by adding WFI to the active pharmaceutical ingredient with swirling until wetted. Transfer the slurry to the stirring Captisol® solution. Rinse the active pharmaceutical ingredient with WFI (3×) and add the rinses to the stirring bulk solution. Stir until the active pharmaceutical ingredient has been dispersed. Stir for no longer than 60 minutes. Some particles may be visible in the manufacturing vessel after stirring for 60 minutes. Maintain the pH of the solution between 4.0-6.0. If the pH drops below the lower limit, 10% NaOH solution may be added to bring the pH into range. Add WFI to the manufacturing vessel to bring the solution to the final batch weight which is calculated based on the desired batch volume and the density of the solution. Measure the pH of the solution and adjust, if necessary, to pH 4.0-6.0 with 10% NaOH. Filter the solution through a sterile 0.22 micron PVDF membrane (Millipore Durapore®) into a sterile receiving vessel. Fill the drug product into sterile vials. Upon completion of filling, stopper and seal the vials. If not dosed within about 4 hours, store all vials at −20° C. The unit formula is shown in Table 5.

TABLE 5

| Unit Formula Active Ingredient | Quantity (mg/mL) |
|---|---|
| Methanesulfonic acid monohydrate[1] salt | 2.6 (Equivalent to 2.0 free base) |
| Other Ingredients[2] | |
| Captisol ® (sulfobutyl ether beta-cyclodextrin, sodium salt) | 120 |
| Water for Injection | q.s. |
| Sodium hydroxide solution[3] | — |

[1]The amount of active pharmaceutical ingredient may be adjusted to take into account the Assay "as is, free base" of the drug substance.
[2]A reasonable variation of +/−10% is allowed for each excipient unless otherwise stated.
[3]Quantity sufficient to adjust pH.

Table 6 below demonstrates the mean plasma concentration following a single 10 mg/kg 1-hour intravenous infusion of 5-(5-(2-(3-aminopropoxy)-6-methoxyphenyl)-1H-pyrazol-3-ylamino)pyrazine-2-carbonitrile methanesulfonic acid monohydrate salt.

TABLE 6

| Time (Hours) | Mean (ng/ml) | S.D. | % CV | n |
|---|---|---|---|---|
| 0.25 | 1060 | 84.1 | 7.9 | 6 |
| 0.5 | 1100 | 68.6 | 6.2 | 6 |
| 1 | 930 | 215 | 23.1 | 6 |
| 1.25 | 319 | 21.1 | 6.6 | 6 |
| 1.5 | 249 | 24.2 | 9.7 | 6 |
| 2 | 178 | 11.5 | 6.5 | 6 |
| 4 | 67.5 | 10.1 | 15.0 | 6 |
| 8 | 30.3 | 2.30 | 7.6 | 6 |
| 24 | 3.00 | 0.331 | 11.0 | 3 |

Abbreviations:
BLQ = Below limit of quantitation of 2 ng/mL,
CV = coefficient of variation,
n = number of animals,
S.D. = standard deviation Table 7 below demonstrates the mean plasma concentration following a single 10 mg/kg 1-hour intravenous infusion of 5-(5-(2-(3-aminopropoxy)-6-methoxyphenyl)-1H-pyrazol-3-ylamino)pyrazine-2-carbonitrile (S)-lactacte monohydrate salt.

TABLE 7

| Time (Hours) | Mean (ng/ml) | S.D. | % CV | n |
|---|---|---|---|---|
| 0.25 | 1110 | 90.3 | 8.1 | 6 |
| 0.5 | 1180 | 79.4 | 6.7 | 6 |
| 1 | 1140 | 107 | 9.4 | 6 |
| 1.25 | 405 | 51.1 | 12.6 | 6 |
| 1.5 | 283 | 28.6 | 10.1 | 6 |
| 2 | 217 | 18.9 | 8.7 | 6 |
| 4 | 73.8 | 5.70 | 7.7 | 6 |
| 8 | 28.6 | 5.06 | 17.7 | 6 |
| 24 | 2.60 | 0.148 | 5.7 | 4 |

I claim:

1. A compound which is 5-(5-(2-(3-aminopropoxy)-6-methoxyphenyl)-1H-pyrazol-3-ylamino)pyrazine-2-carbonitrile (S)-lactate monohydrate.

2. The compound according to claim 1 in crystalline form.

3. The compound according to claim 2, wherein the crystalline form is characterized by a X-ray powder diffraction pattern (CuKa radiation, $\lambda$=1.54060 Å) comprising a peak at 12.6, and one or more peaks at 24.8, 25.5, 8.1, 6.6, 12.3, and 16.3 (2θ+/−0.2°).

4. A pharmaceutical composition comprising 5-(5-(2-(3-aminopropoxy)-6-methoxyphenyl)-1H-pyrazol-3-ylamino) pyrazine-2-carbonitrile (S)-lactate monohydrate and one or more pharmaceutically acceptable carriers, diluents, or excipients.

5. The pharmaceutical composition of claim 4, wherein 5-(5-(2-(3-aminopropoxy)-6-methoxyphenyl)-1H-pyrazol-3-ylamino)pyrazine-2-carbonitrile (S)-lactate monohydrate is in crystalline form.

6. The pharmaceutical composition of claim 5, wherein the crystalline form is characterized by a X-ray powder diffraction pattern (CuKa radiation, $\lambda$=1.54060 Å) comprising a first peak at 12.6, and one or more peaks at 24.8, 25.5, 8.1, 6.6, 12.3, and 16.3 (2θ+/−0.2°).

7. A method of treating cancer comprising: administering to a patient in need thereof an effective amount of a compound which is 5-(5-(2-(3-aminopropoxy)-6-methoxyphenyl)-1H-pyrazol-3-ylamino)pyrazine-2-carbonitrile (S)-lactate monohydrate.

8. The method of claim 7, wherein the compound is in crystalline form.

9. The method of claim 8, where the crystalline form is characterized by a X-ray powder diffraction pattern (CuKa radiation, $\lambda$=1.54060 Å) comprising a peak at 12.6, and one or more peaks at 24.8, 25.5, 8.1, 6.6, 12.3, and 16.3 (2θ+/−0.2°).

10. The method according to claim 7, wherein the compound is administered with one or more pharmaceutically acceptable carriers, diluents, or excipients.

11. The method according to claim 7, wherein the method further comprises administering ionizing radiation.

12. The method according to claim 7, wherein the method further comprises administering one or more chemotherapy agents.

13. The method according to claim 7, wherein the method further comprises administering a chemotherapy agent selected from the group consisting of 5-fluorouracil, hydroxyurea, gemcitabine, methotrexate, pemetrexed, doxorubicin, etoposide, cetuximab, cisplatin, taxol, and combinations thereof.

* * * * *

UNITED STATES PATENT AND TRADEMARK OFFICE
CERTIFICATE OF CORRECTION

PATENT NO. : 10,189,818 B2  
APPLICATION NO. : 15/513185  
DATED : January 29, 2019  
INVENTOR(S) : Alessandra B. Ennett-Shepard Page 1 of 1

It is certified that error appears in the above-identified patent and that said Letters Patent is hereby corrected as shown below:

On the Title Page

Column 1 (Title), Line 1, delete "-AMINOPROPDOXY)-" and insert -- -AMINOPROPOXY)- --, therefor.

Column 1 (Title), Line 3, delete "-CARBONITFILE" and insert -- -CARBONITRILE --, therefor.

In the Specification

Column 1, Line 1, delete "-AMINOPROPDOXY)-" and insert -- -AMINOPROPOXY)- --, therefor.

Column 1, Line 3, delete "-CARBONITFILE" and insert -- -CARBONITRILE --, therefor.

Signed and Sealed this  
Second Day of April, 2019

Andrei Iancu  
*Director of the United States Patent and Trademark Office*